United States Patent [19]

Vidal et al.

[11] Patent Number: 5,735,445
[45] Date of Patent: Apr. 7, 1998

[54] SURGICAL STAPLER

[75] Inventors: Claude A. Vidal, Santa Barbara; Alan K. Plyley, Goleta, both of Calif.

[73] Assignee: United States Surgical Corporation, Norwalk, Conn.

[21] Appl. No.: 818,086

[22] Filed: Mar. 14, 1997

Related U.S. Application Data

[63] Continuation of Ser. No. 399,929, Mar. 7, 1995, abandoned.

[51] Int. Cl.$^6$ ................................................ A61B 17/072
[52] U.S. Cl. ................................ 227/175.4; 227/176.1; 227/19
[58] Field of Search .......................... 227/175.2, 175.3, 227/175.4, 176.1, 19, 8

[56] References Cited

U.S. PATENT DOCUMENTS

| | | |
|---|---|---|
| Re. 34,519 | 1/1994 | Fox et al. . |
| D. 283,733 | 5/1986 | Rawson et al. . |
| 2,174,219 | 9/1939 | Balma . |
| 2,246,647 | 6/1941 | Vancura . |
| 3,079,606 | 3/1963 | Bobrov et al. . |
| 3,079,608 | 3/1963 | Babkin . |
| 3,080,564 | 3/1963 | Strekopytov et al. . |
| 3,252,643 | 5/1966 | Strekopytov et al. . |
| 3,490,675 | 1/1970 | Green et al. . |
| 3,499,591 | 3/1970 | Green . |
| 3,675,688 | 7/1972 | Bryan et al. . |
| 3,844,289 | 10/1974 | Noiles . |
| 4,086,926 | 5/1978 | Green et al. . |
| 4,202,480 | 5/1980 | Annett . |
| 4,256,251 | 3/1981 | Moshofsky . |
| 4,304,236 | 12/1981 | Conta et al. . |
| 4,331,276 | 5/1982 | Bourque . |
| 4,354,628 | 10/1982 | Green . |
| 4,391,401 | 7/1983 | Moshofsky . |
| 4,473,077 | 9/1984 | Noiles et al. . |
| 4,480,640 | 11/1984 | Becht . |
| 4,500,025 | 2/1985 | Skwor . |
| 4,513,746 | 4/1985 | Aranyi et al. . |
| 4,519,532 | 5/1985 | Foslien . |
| 4,520,817 | 6/1985 | Green . |
| 4,522,327 | 6/1985 | Korthoff et al. . |
| 4,523,695 | 6/1985 | Braun et al. . |
| 4,527,724 | 7/1985 | Chow et al. . |
| 4,540,110 | 9/1985 | Bent et al. . |
| 4,566,620 | 1/1986 | Green et al. . |
| 4,569,346 | 2/1986 | Poirier . |
| 4,573,622 | 3/1986 | Green et al. . |
| 4,576,167 | 3/1986 | Noiles . |
| 4,580,712 | 4/1986 | Green . |

(List continued on next page.)

FOREIGN PATENT DOCUMENTS

| | | |
|---|---|---|
| 2542188 | 9/1984 | European Pat. Off. . |
| 0136950 | 4/1985 | European Pat. Off. . |
| 0220029 | 4/1987 | European Pat. Off. . |
| 0273468 | 7/1988 | European Pat. Off. . |
| 0537571 | 4/1993 | European Pat. Off. . |
| 2141066 | 12/1984 | United Kingdom . |

OTHER PUBLICATIONS

"Auto Suture® Poly CS™–57 Disposable Surgical Stapler", United States Surgical Corporation, 1988.

"Proximate RL Plus Reloadable Linear Stapler", Ethicon, Inc., 1990.

*Primary Examiner*—Rinaldi I. Rada
*Assistant Examiner*—Boyer Ashley

[57] ABSTRACT

A surgical stapler having a supporting frame, replaceable staple cartridge, an anvil, a mechanism for approximating the cartridge relative to the anvil, and a mechanism for firing the device so as to crimp the staples against the anvil in a manner to enable the surgeon to substantially simultaneously place one or more rows of surgical staples in organs or tissue. The device, while at all times permitting approximation of the cartridge relative to the anvil, provides a novel lockout feature for positively preventing retiring if the staple cartridge is spent. In this way, unlike the prior art devices, the device of the present invention can be used as a clamping mechanism even after the staples have been fired.

32 Claims, 9 Drawing Sheets

U.S. PATENT DOCUMENTS

| | | |
|---|---|---|
| 4,585,153 | 4/1986 | Failla et al. . |
| 4,591,085 | 5/1986 | Di Giovanni . |
| 4,592,498 | 6/1986 | Braun et al. . |
| 4,597,517 | 7/1986 | Wagdy . |
| 4,605,004 | 8/1986 | Di Giovanni et al. . |
| 4,610,383 | 9/1986 | Rothfuss et al. . |
| 4,633,861 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,715,520 | 12/1987 | Roehr, Jr. et al. . |
| 4,728,020 | 3/1988 | Green et al. . |
| 4,807,628 | 2/1989 | Peters et al. . |
| 4,809,898 | 3/1989 | Gassner et al. . |
| 4,821,942 | 4/1989 | Richards et al. . |
| 4,850,355 | 7/1989 | Brooks et al. . |
| 4,869,414 | 9/1989 | Green et al. . |
| 4,892,244 | 1/1990 | Fox et al. .................................. 227/8 |
| 4,938,408 | 7/1990 | Bedi et al. . |
| 4,941,623 | 7/1990 | Pruitt . |
| 4,955,959 | 9/1990 | Tompkins et al. . |
| 4,964,559 | 10/1990 | Deniega et al. . |
| 5,018,657 | 5/1991 | Pedlick et al. . |
| 5,031,814 | 7/1991 | Tompkins et al. . |
| 5,071,052 | 12/1991 | Rodak et al. . |
| 5,100,042 | 3/1992 | Gravener et al. . |
| 5,106,008 | 4/1992 | Tompkins et al. .................. 227/178 |
| 5,129,570 | 7/1992 | Schulze et al. .................... 227/176 |
| 5,156,315 | 10/1992 | Green et al. . |
| 5,395,034 | 3/1995 | Allen et al. . |
| 5,413,267 | 5/1995 | Solyntjes et al. ................ 227/175.4 |
| 5,458,279 | 10/1995 | Plyley . |
| 5,462,215 | 10/1995 | Viola et al. . |
| 5,470,008 | 11/1995 | Rodak . |
| 5,470,009 | 11/1995 | Rodak . |

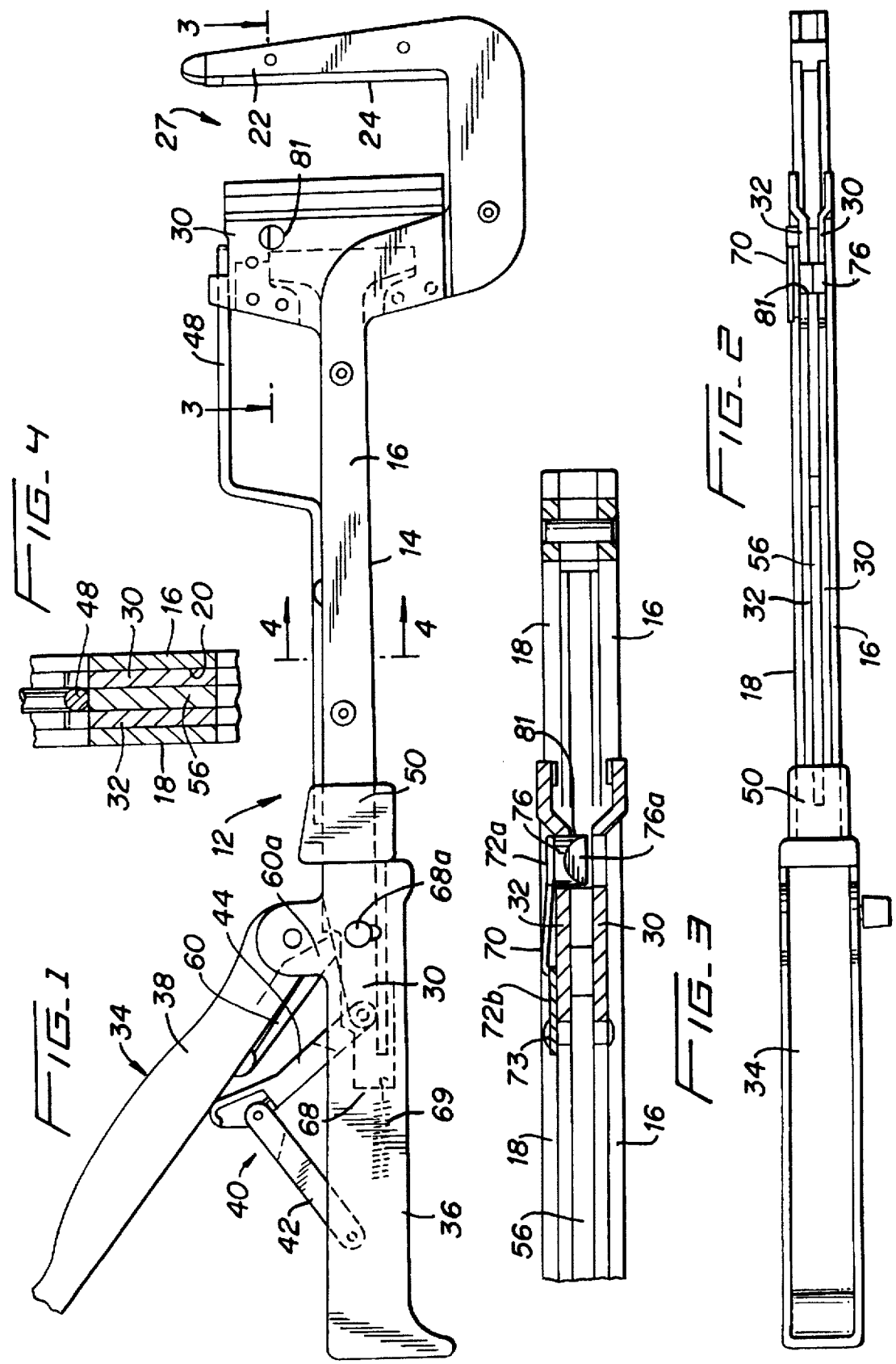

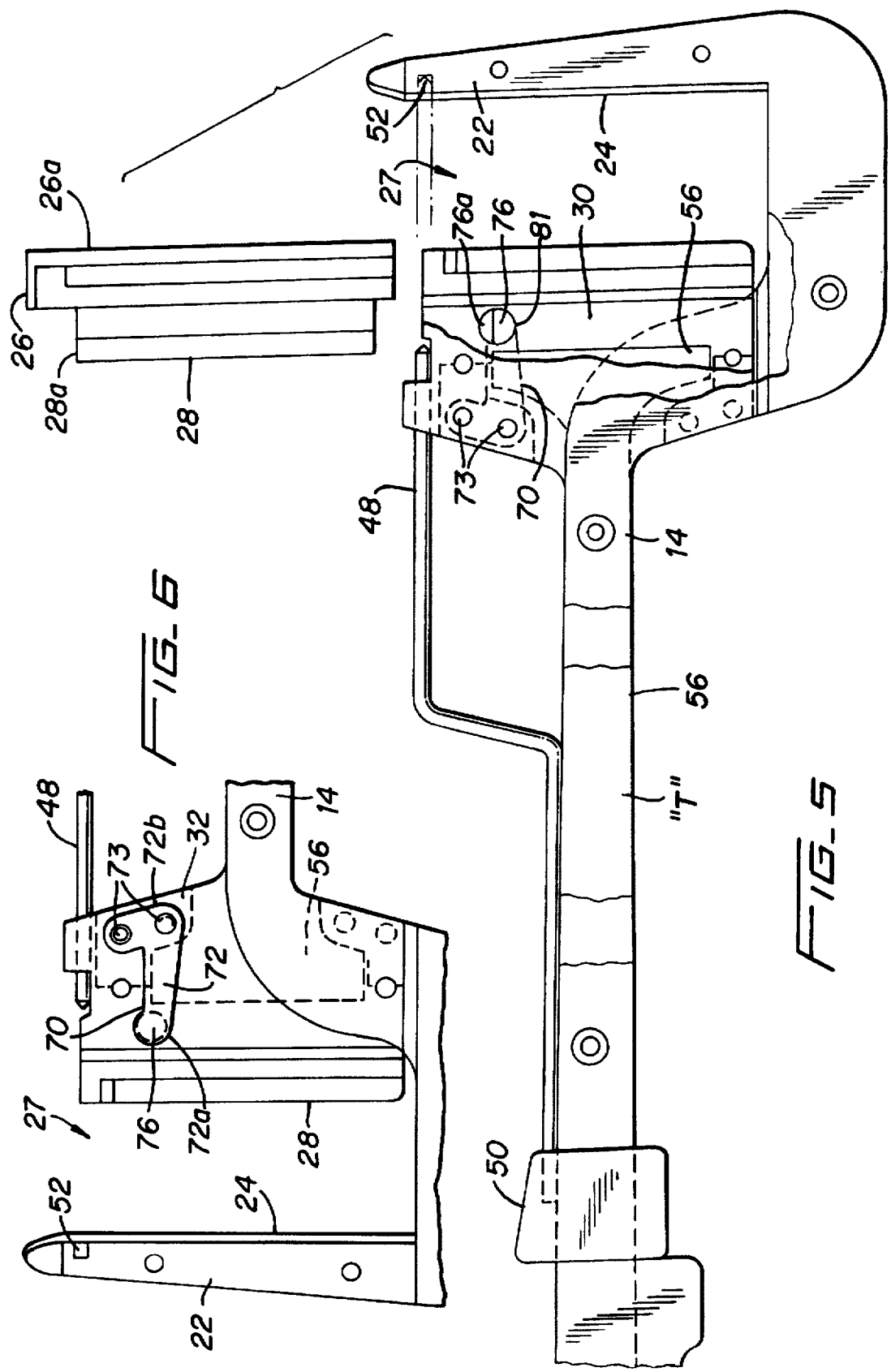

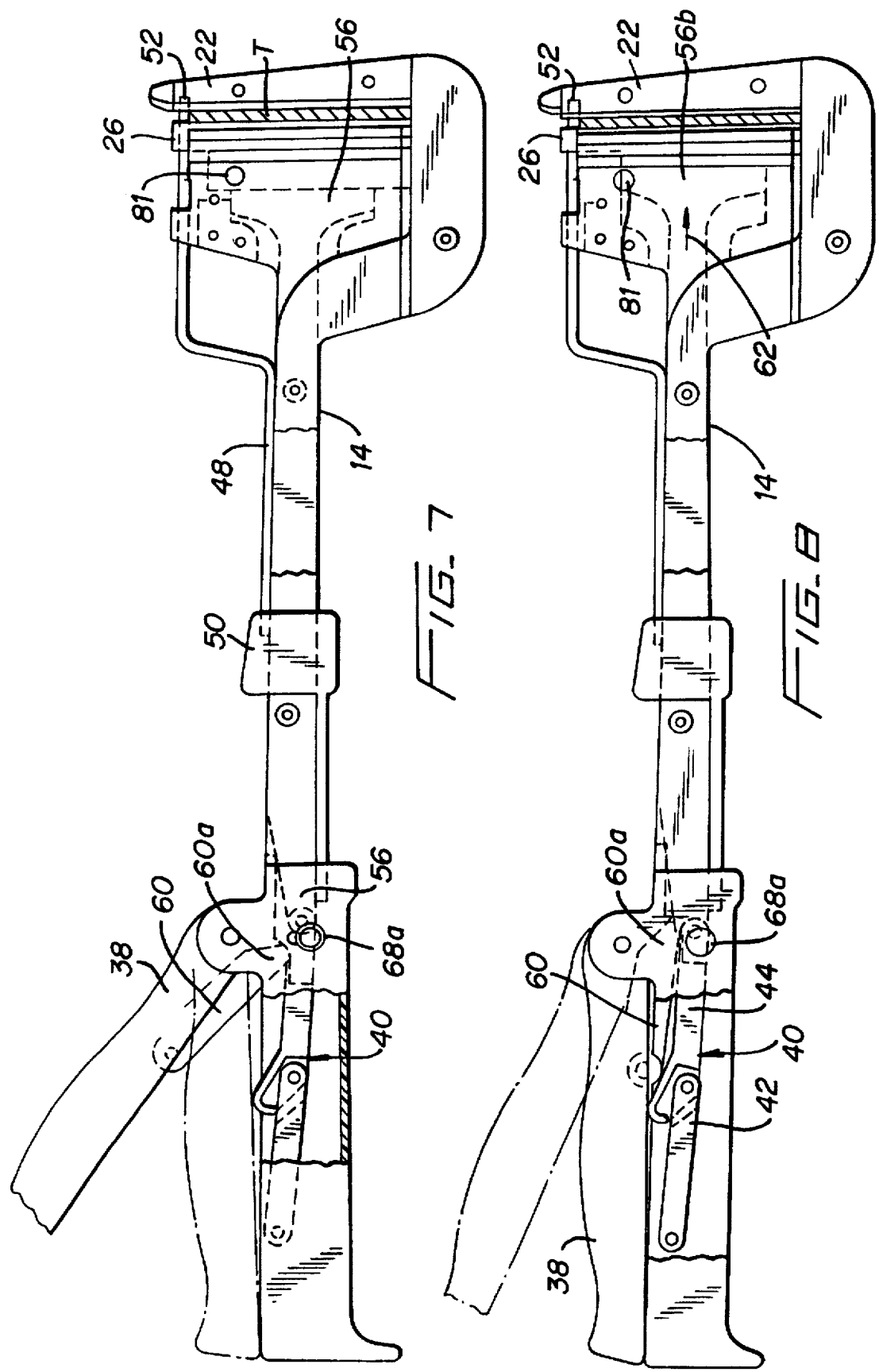

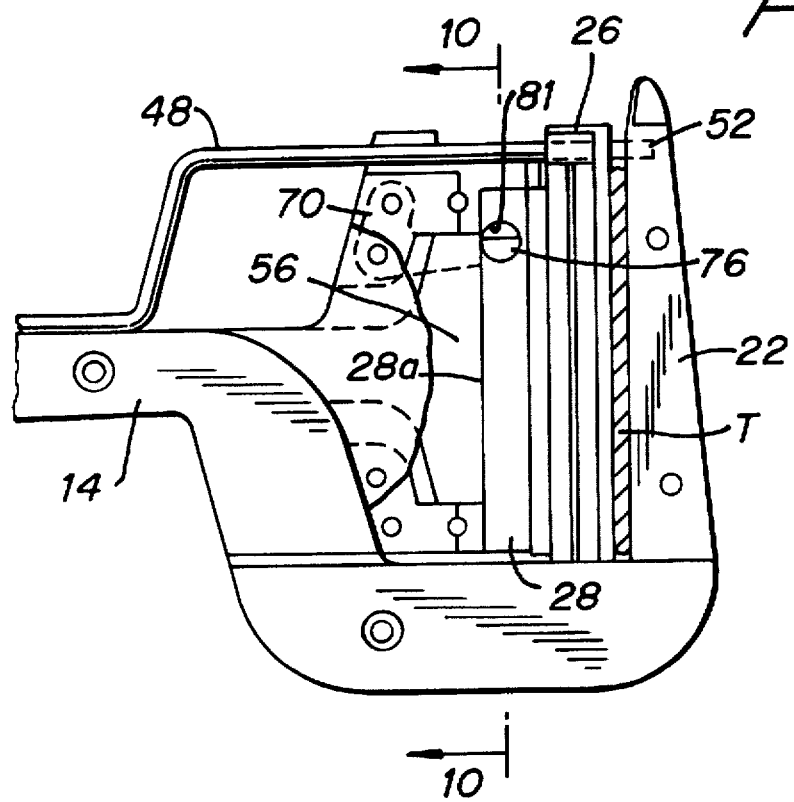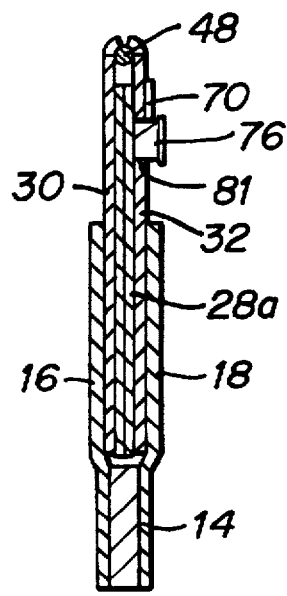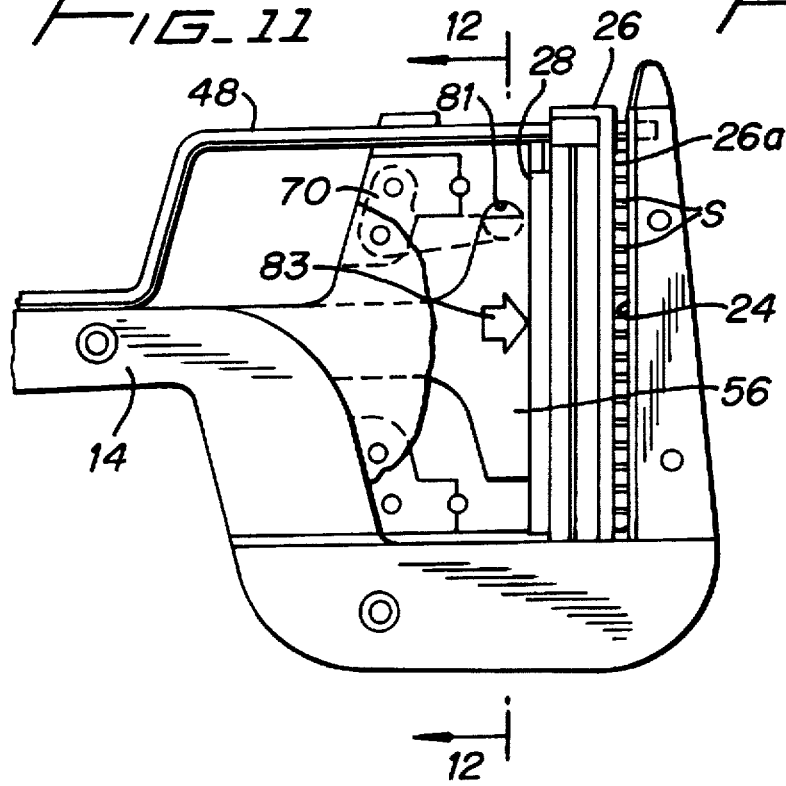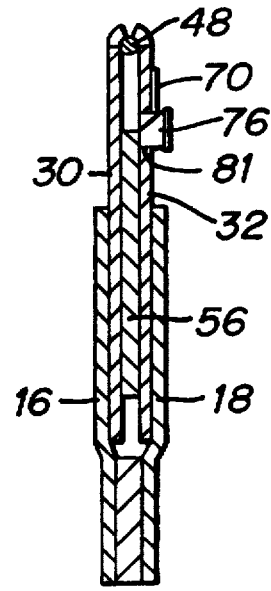

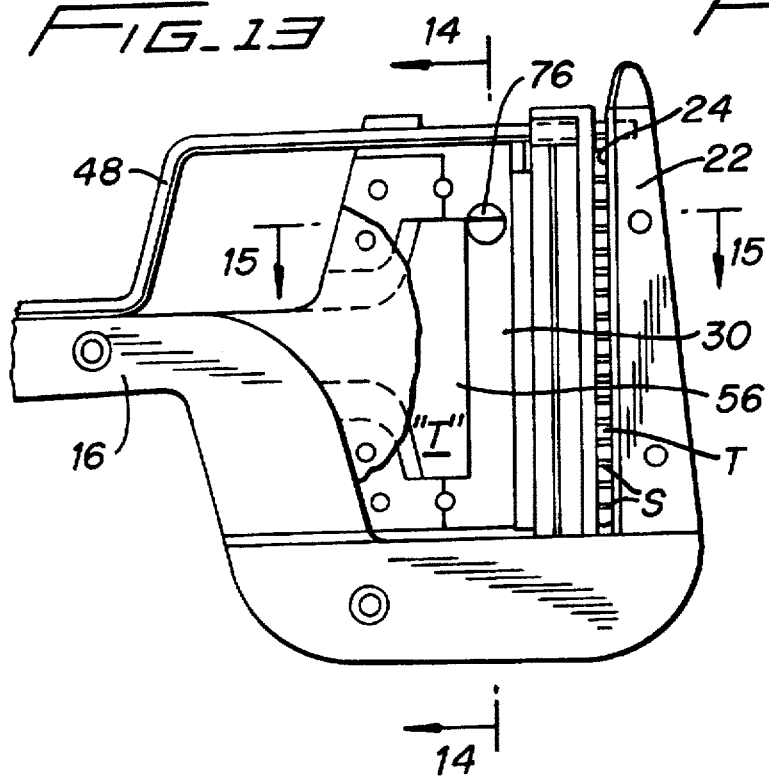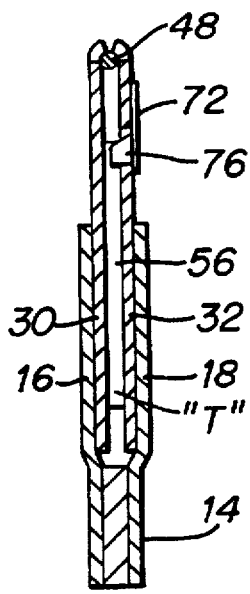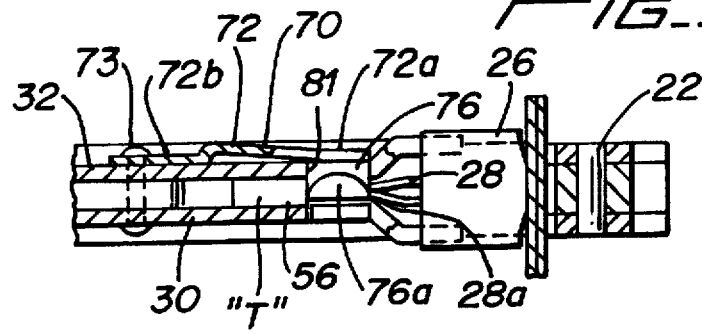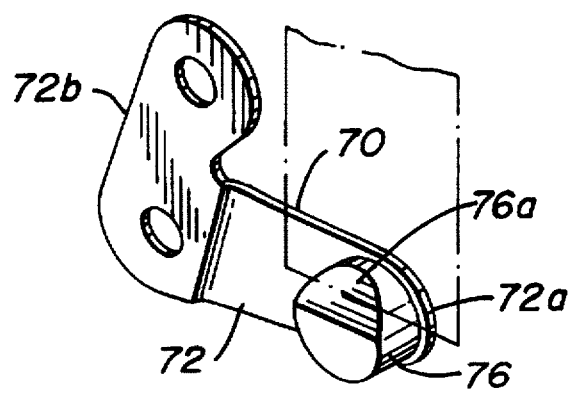

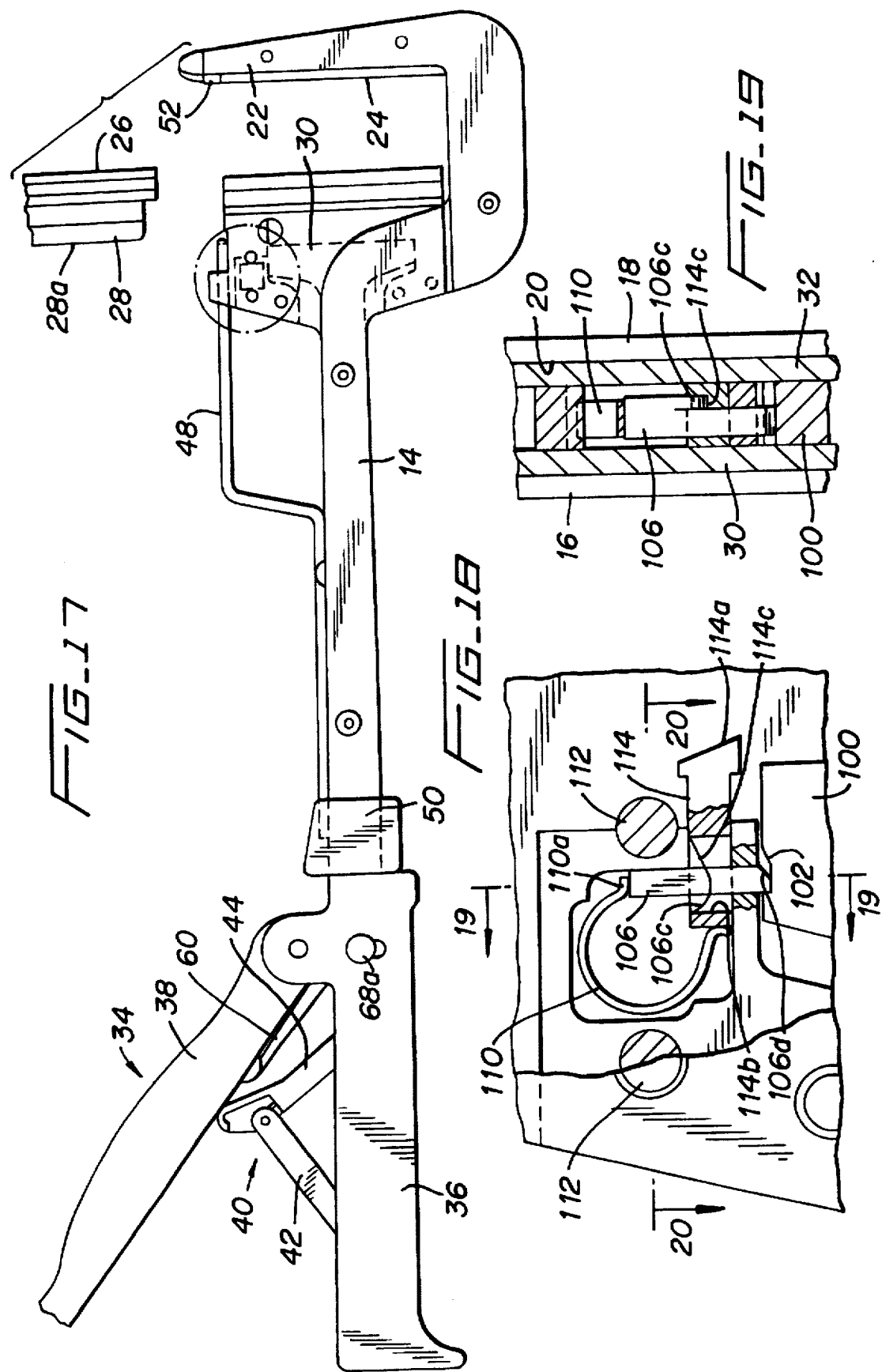

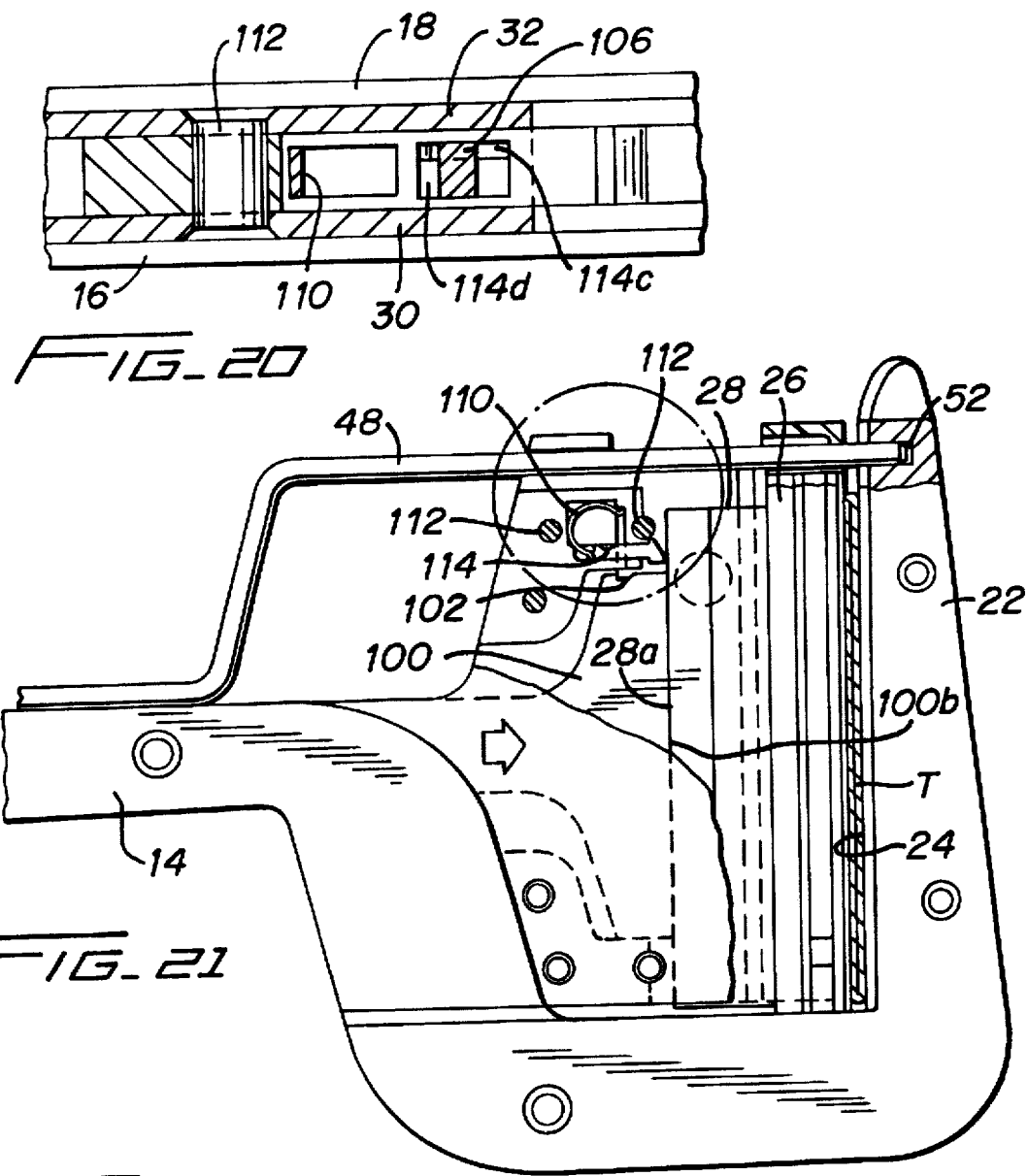

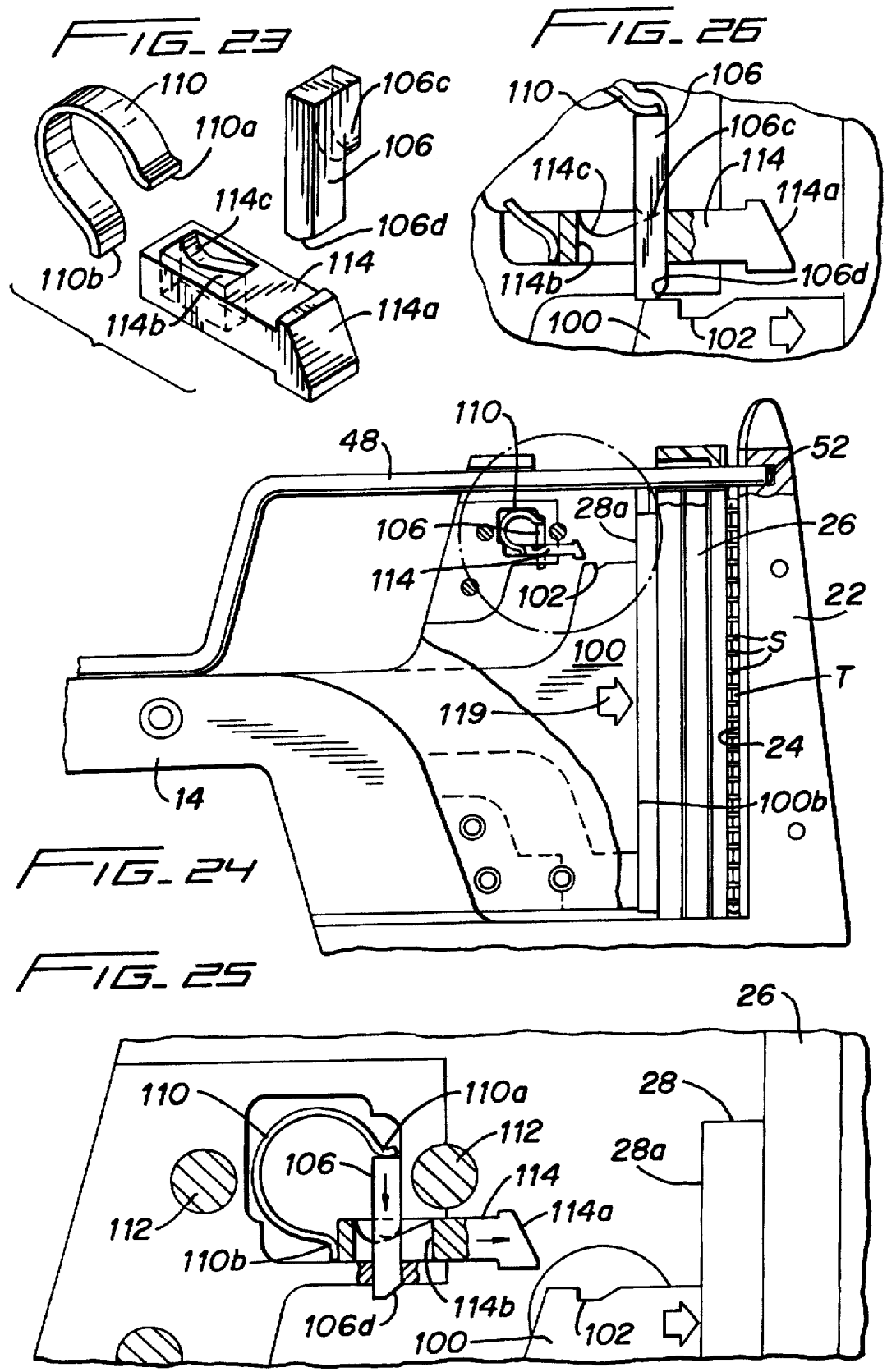

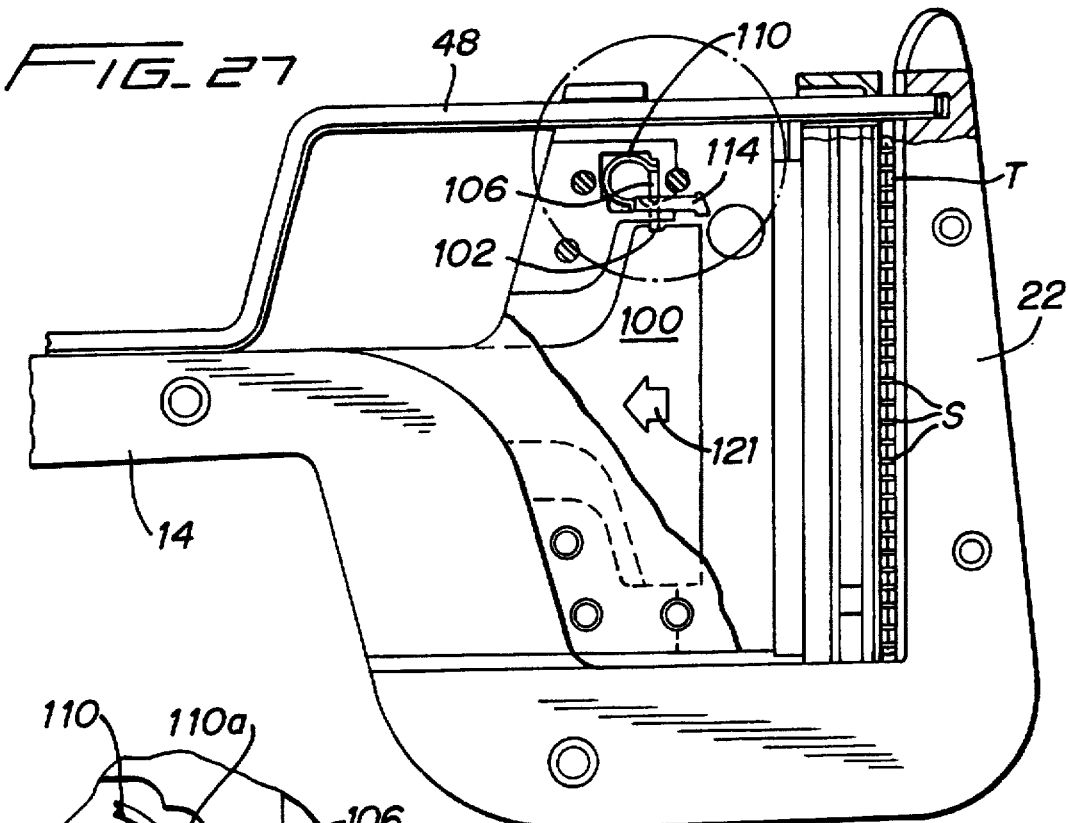
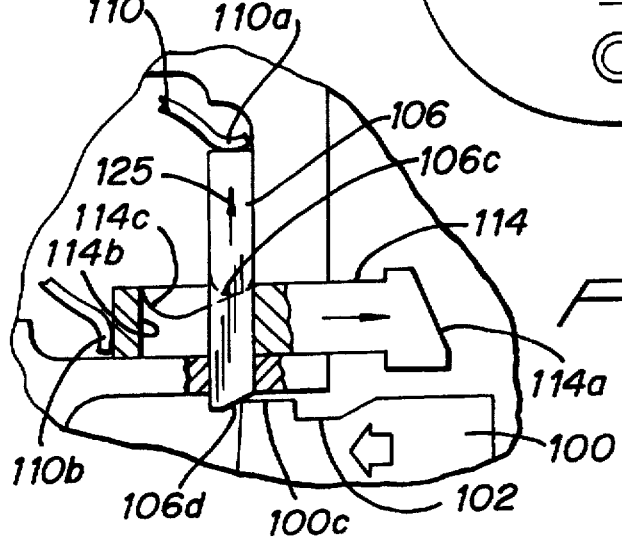
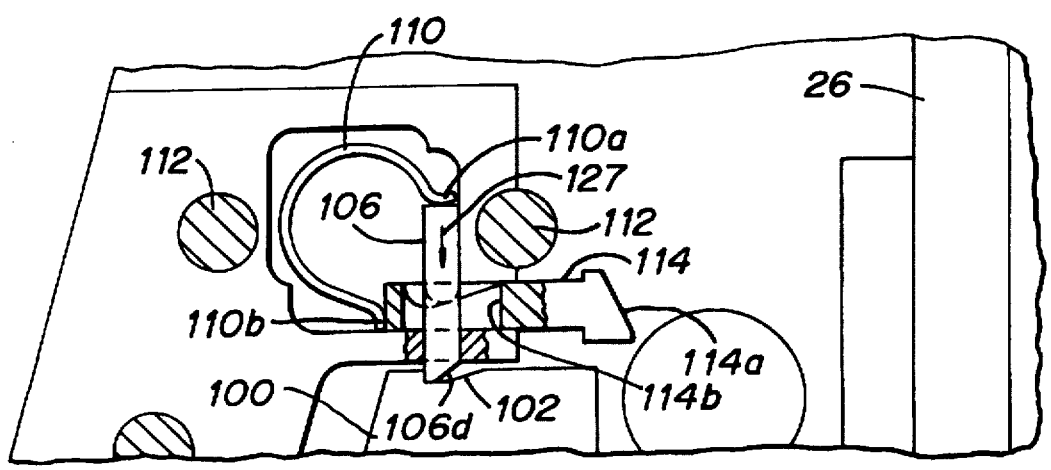

5,735,445

SURGICAL STAPLER

This is a continuation of U.S. application Ser. No. 08/399,929, filed on Mar. 7, 1995, now abandoned.

FIELD OF THE INVENTION

The present invention relates generally to surgical stapling devices. More particularly, the invention concerns a novel surgical stapler that embodies a lockout mechanism that positively prevents the surgeon from inadvertently attempting to reuse an empty staple cartridge.

BACKGROUND

Surgical staplers are frequently used in surgical procedures for suturing body tissue as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. The staples are generally made of metal, although they can be made from polymers, copolymers and similar materials. During the typical suturing process, pusher bars within the cartridge are controllably advanced by the actuator mechanism in a manner to urge the staples out of the cartridge, through the tissue and forcibly against the anvil.

Possibly the most frequently used type of surgical stapler is the linear stapler, which is a device that enables the surgeon to place one to several (typically 2 to 4) rows of surgical staples in body tissue or organs. By way of example, a typical procedure is a pneumonectory, that is, a removal of a portion of a patient's lungs. The linear stapler can be used several times during this procedure, including its use for the occlusion of the pulmonary artery prior to its resection. For this latter use, the surgeon clamps the jaws of the stapler across the artery, fires the staples and, prior to reopening the stapler, cuts the artery, using the edge of the staple jaws as a guide. If the scrub nurse forgets to reload the stapler with a fresh cartridge before the artery resection, the surgeon will become aware of it only when he or she reopens the jaws of the stapler, that is, after he or she has already cut the artery. In such a case, a severe hemorrhage would ensue. Thus, a lockout mechanism should be provided to reduce the chances for such an accident to occur. An aspect of the present invention is to provide an apparatus that includes such a lockout mechanism that will effectively restrict the chances for the occurrence of such an accident. More specifically, the invention provides a linear surgical stapler with a moving lock member, biased in such a way that it will disable the staple firing function of the stapler if the staple cartridge has already been fired.

Several attempts have been made in the past to provide surgical staplers that embody some type of lockout mechanism that prevents retiring of a spent staple cartridge. Examples of the replete art of staplers with lockout devices include those described in EP 545029A1; PCT International Publication Number WO 92/10976; U.S. Pat. No. 5,106,008 issued to Tompkins, et al.; U.S. Pat. No. 5,129,570 issued to Schulze, et al.; U.S. Pat. No. 5,307,976 to Olson et al.; U.S. Pat. No. 5,318,221 to Green et al.; and U.S. Pat. No. 4,892,244 issued to Fox, et al.

EPO Publication Numbers, 489,436A1 and 537572A2 (filed by United States Surgical Corporation) also disclose linear staplers having locking mechanisms that prevent re-approximation of the staple cartridge towards the anvil after the cartridge is fired and moved away from the anvil. A device sold by 3M Health Care of St. Paul, Minn. under the designation "Precise-PI-55" and generally disclosed in EP 514139A2 also represents an example of a prior art linear stapler having a mechanism to prevent re-approximation of the staple cartridge relative to the anvil after the staples are fired.

The present invention is directed toward providing a highly novel, improved surgical stapling apparatus that offers significant advantages over the aforementioned prior art devices. More particularly, unlike the prior art devices, the apparatus of the present invention uniquely permits re-approximation of the staple cartridge towards the anvil after firing of the staples so that the device can be used as a clamp, but at the same time prevents any attempt to fire the empty staple cartridge. This feature enables the device to safely be used to clamp and reclamp tissue even though the surgeon is positively advised that the staple cartridge has been spent. Additionally, while many of the prior art devices are quite complex, the apparatus of the present invention is of simple construction, is easy to use and yet is extremely reliable.

SUMMARY OF THE INVENTION

It is an object of the present invention to provide a surgical stapler of the character having a supporting frame, a replaceable staple cartridge, an anvil, means for approximating the cartridge relative to the anvil, and means for firing the device so as to crimp the staples against the anvil in a manner to enable the surgeon to substantially simultaneously place one or more rows of surgical staples in organs or tissue. The device, while at all times permitting approximation of the cartridge relative to the anvil, provides novel lockout means for positively preventing retiring of the device if the staple cartridge is spent. In this way, unlike the prior art devices, the device of the present invention can be used as a clamping mechanism even after the staples have been fired.

It is another object of the invention to provide a surgical stapler of the aforementioned character which includes a novel locking mechanism that positively prevents advancement by the surgeon of the staple crimping member of the firing mechanism even though the staple cartridge is disposed proximate the anvil.

Another object of the invention is to provide, in one embodiment of the invention, a surgical stapler of the type described in the preceding paragraph in which the locking mechanism is carried internally of the frame.

Another object of the invention is to provide a surgical stapler of the character described in which the locking means is automatically disarmed by the insertion into the device of a fresh staple cartridge.

Another object of the invention is to provide a surgical stapler that, following staple firing, can be used to reclamp the tissue at a location proximate the stapled closure to permit ease of cauterization or suturing should fluid oozing be detected.

Another object of the invention is to provide a surgical stapler which is highly versatile, easy to use, and is of simple construction.

BRIEF DESCRIPTION OF THE DRAWINGS

FIG. 1 is a side-elevational view of one form of the linear stapling apparatus of the present invention.

FIG. 2 is a top view of the apparatus.

FIG. 3 is an enlarged, cross-sectional view taken along lines 3—3 of FIG. 1.

FIG. 4 is an enlarged, cross-sectional view taken along lines 4—4 of FIG. 1.

FIG. 5 is an enlarged, fragmentary, side-elevational view of the forward portion of the stapling apparatus showing the staple cartridge and associated pusher member in position for insertion into the supporting frame of the device.

FIG. 6 is a fragmentary, side-elevational view of the opposite side of the forward portion of the apparatus showing the staple cartridge and associated pusher member in position within the supporting frame of the device.

FIG. 7 is a side-elevational view similar to FIG. 1, but showing the removable staple cartridge having been advanced by the operating means to a position proximate the anvil of the device.

FIG. 8 is a side-elevational view similar to FIG. 7, but showing the location of the component parts of the apparatus after the device has been fired to urge the staples from the staple cartridge into pressural engagement with the anvil.

FIG. 9 is an enlarged side-elevational view of the apparatus showing the staple cartridge of the device having been moved into close proximity with the anvil and in clamping engagement with tissue disposed between the staple cartridge and the face of the anvil.

FIG. 10 is a cross-sectional view taken along lines 10—10 of FIG. 9.

FIG. 11 is a fragmentary, side-elevational view similar to FIG. 10, but showing the location of the component parts of the device following the firing step wherein the pusher member has been urged inwardly of the staple cartridge to force the staples contained therein, through the tissue and into pressural engagement with the face of the anvil.

FIG. 12 is a cross-sectional view taken along lines 12—12 of FIG. 11.

FIG. 13 is a fragmentary, side-elevational view similar to FIG. 11, but showing the apparatus in a safe configuration with the locking means of the invention blocking forward movement of the actuator, or "T" bar of the device.

FIG. 14 is a cross-sectional view taken along lines 14—14 of FIG. 13.

FIG. 15 is an enlarged, cross-sectional view taken along lines 15—15 of FIG. 13 further illustrating the locking means in the safe or locked position.

FIG. 16 is a greatly enlarged, generally perspective view of the locking element of the form of the apparatus shown in FIGS. 1 through 15.

FIG. 17 is a side-elevational view of an alternate form of the linear stapling apparatus of the present invention.

FIG. 18 is an enlarged view partly in cross-section of the area designated as 18—18 in FIG. 17.

FIG. 19 is an enlarged, cross-sectional view taken along lines 19—19 of FIG. 18.

FIG. 20 is a cross-sectional view taken along lines 20—20 of FIG. 18.

FIG. 21 is an enlarged, fragmentary, side-elevational view of the forward portion of the stapling apparatus of the alternate form of the invention showing the staple cartridge and associated pusher member in approximated position showing tissue clamped between the staple cartridge and the anvil.

FIG. 22 is an enlarged, fragmentary view of the portion of the apparatus generally designated as 22—22 of FIG. 21.

FIG. 23 is a generally perspective, exploded view of the novel locking mechanism of this alternate form of the invention.

FIG. 24 is a side-elevational view similar to FIG. 21, but showing the location of the component parts of the apparatus after the device has been fired to urge the staples from the staple cartridge into pressural engagement with the anvil.

FIG. 25 is an enlarged, side-elevational view, partly in cross section, of the area designated as 25—25 of FIG. 24.

FIG. 26 is an enlarged, fragmentary view of a portion of the locking mechanism showing it in a retracted, unlocked position.

FIG. 27 is a fragmentary, side-elevational view similar to FIG. 23, but showing the apparatus in a safe configuration with the locking means of the invention blocking forward movement of the actuator, or "T" bar of the device.

FIG. 28 is an enlarged, fragmentary view partly in cross section showing the lifting of the locking pin as the T-bar is retracted.

FIG. 29 is an enlarged view, partly in. cross section illustrating the locking pin in a downward, locking configuration with a notch formed in the T-bar.

DESCRIPTION OF THE INVENTION

Referring to the drawings and particularly to FIGS. 1 through 4, one form of the apparatus for simultaneously emplacing a plurality of surgical staples into tissue and organs is there shown and generally designated by the numeral 12. The apparatus comprises an elongated supporting frame 14 having first and second spaced walls 16 and 18 defining an interior space 20. The anvil portion 22 of the apparatus, which includes a staple-engaging face 24 is disposed at the forward end of the supporting frame 14. Removably receivable within the supporting frame is a staple cartridge 26 (FIG. 5) which contains a plurality of surgical staples that are adapted to pass through the tissue to be stapled and then be crimped against face 24 of anvil 22 in a manner presently to be described. As best seen by referring to FIG. 5, a pusher member is associated with cartridge 26 for movement between a first extended position as shown in FIG. 5 to a second fired position shown in FIG. 11. During firing, pusher member 28 engages the staples "S" contained within staple cartridge 26 and drives them forwardly into pressural engagement with face 24 of anvil 22. As the staples are substantially simultaneously driven from the staple cartridge, they will engage the anvil face and typically crimp into a crimped shaped roughly corresponding to the shape of the letter "B". As the staples "S" are appropriately crimped, they will, of course, join together the layers of tissue or organ disposed between lace 24 of the anvil and the forward face 26a of the staple cartridge.

When the staple cartridge and cooperating pusher member are disposed in a spaced-apart relationship with face 24 of anvil 22, tissue or human organ can be placed in the open space 27 between the operating mechanism of the device and face 24 of the anvil. After the tissue has been appropriately positioned between the staple cartridge and the anvil, approximation means are provided to controllably move the staple cartridge 26, along with pusher 28, forwardly of the apparatus into proximity with face 24 of anvil 22. As shown in FIGS. 3 and 4, the approximation means of the invention here comprises a pair of spaced-apart approximation members 30 and 32 which are disposed between side walls 16 and 18 and are slidably movable with respect thereto from a first retracted position shown in FIGS. 1, 2, and 3 to a forward, approximation position shown in FIG. 7.

In the present form of the invention, the approximation means also includes a handle assembly 34 which comprises a fixed handle portion 36 and a movable handle portion 38 which is pivotally connected to fixed handle portion 36 in the manner best seen in FIG. 1. The approximation means further includes a linkage assembly 40 made up of pivotally interconnected first and second link elements 42 and 44. As indicated in FIG. 7, as handle portion 38 is moved into its downward or actuated configuration, linkage assembly 40 will move from the angled configuration shown in FIG. 1 to the straight line configuration shown in FIG. 7 causing approximation members 30 and 32 to move forwardly of the device in the manner indicated in FIG. 7.

As best seen by referring to FIGS. 1 and 7, prior to the approximation step, an elongated guide rod 48 is moved forwardly using a gripping member 50 from the retracted position shown in FIG. 1 to the forward position shown in FIG. 7. Guide rod 48 in its forward position engages an opening 52 formed in anvil 22 and functions to maintain alignment between the staple cartridge and the anvil 22. As can be observed by referring to FIG. 7, at the time of advancement of the guide rod 48, the tissue or other material to be stapled, which is generally designated by the letter "T" is in position between the staple cartridge and the anvil.

After the staple cartridge and its associated pusher member have been moved into close proximity with anvil 22 and locked in a clamping relationship with tissue "T", by linkage assembly 40, the apparatus is in condition for the firing or staple crimping operation. This staple-firing step is accomplished by the operating means of the invention which means is carried by the supporting frame and here comprises an operating member or generally "T" shaped bar 56 which is disposed intermediate operating members 30 and 32 (FIG. 4). Operating bar 56 is movable between members 30 and 32 from a first retracted position shown in FIG. 7 to a second advanced or fired position shown in FIG. 8. The operating or T-bar 56 includes a forward face 56b (FIG. 8) which engages wing-like, inwardly bent forward portions 28a of pusher member 28 (FIG. 15) so as to urge the pusher member inwardly of the staple cartridge 26 with sufficient force to engage the staples contained within the staple cartridge and drive them forwardly against face 24 of the anvil. As the staples engage the anvil face, they will be uniformly crimped in a manner to secure together the tissue layers "T" disposed between the staple cartridge assembly and face 24 of anvil 22.

In the form of the invention shown in the drawings, this operating means, in addition to T-bar 56, comprises a second operating link 60 which is pivotally connected to handle portion 38. Operating link 60 includes an end portion which is movable from the position shown in FIG. 1 to the position shown in with handle portion 36. As the handle portions are squeezed together, end 60a of operating link 60 will urge operating member 56 slidably forwardly between members 30 and 32 in the manner shown by the arrow 62 in FIG. 8. This forward movement will cause pusher member 28 to move inwardly of staple cartridge 26 and into engagement with the staples contained therein.

Referring next to FIGS. 7 and 8, it is to be noted that following the approximation step and during the firing step, linkage 40 is releasably maintained in the aligned configuration shown in FIG. 8 by a release assembly 68 which is carried by the supporting frame. As previously discussed, during the firing step, handle 38 is moved into the upward position and then, once again, pivoted downwardly against handle portion 36. Between the approximation step and the firing step, operating link 60 is permitted to move into an operating position wherein it can act upon T-bar 56 to urge it forwardly of the apparatus upon the second depression of handle 38. Following the firing step, a spring 69 carried within the handle assembly will automatically retract the T-bar. Operation of the release assembly 68, which includes slidable button 68a and a suitable biasing means, will cause retraction of the actuation members and automatically cause the return of link assembly 40 to its starting position shown in FIG. 1. It is to be understood that various types of linkage arrangements and release mechanisms of a character well understood by those skilled in the art can be used to sequentially advance and retract members 30 and 32 as well as member 56 during the approximation and firing step.

The general clamping and firing operation of the stapler 12 discussed above is similar to the stapler described in EPO 514139 (the entire contents of which are herein expressly incorporated by reference). Unlike the stapler described in EP 514139 and forming an important aspect of the present invention is the provision of novel locking means for preventing movement of the operating, or T-bar 56, toward its second firing position following the initial firing of the staples. The locking means here comprises a locking element 70 of the configuration shown in FIG. 16. This locking element is connected to approximation member 32 and is adapted for movement from a first position relative to member 32 to a second position wherein the locking element blocks movement of the T-bar 56 forwardly of the apparatus.

As best seen in FIG. 16, the locking element of this form of the invention comprises a strip of resiliently deformable material 72 having first and second ends 72a and 72b. First end 72b is connected to member 32 by rivets or other appropriate fasteners 73 in the manner best seen in FIGS. 3 and 15 (see also FIG. 6). Connected to second end 72a of locking element 70, is a generally cylindrically shaped protuberance 76 having a sloping face 76a formed thereon. Element 72 functions as a biasing means for continuously urging protuberance 76 inwardly of the interior space between members 30 and 32 in the manner shown in FIG. 3.

With the device in the configuration shown in FIGS. 3 and 5, insertion into the supporting frame of the assemblage made up of the staple cartridge 26 and the pusher member 28 will cause pusher member 28 to engage the sloping face 76a of locking member 70 moving it outwardly within an aperture 81 formed in member 32 against the urging of spring element 70. It is important to observe that, when the component parts of the operating mechanism of the device are in the configuration shown in FIG. 3, forward movement of the T-bar member 56 is blocked by head 76 of the locking mechanism. However, upon insertion of the staple cartridge and pusher assembly into the device, blocking head 76 will be cammed outwardly and forward movement of T-bar 56 toward the staple cartridge will be unobstructed.

Turning particularly to FIGS. 9 and 10 wherein the apparatus is shown after the approximation step and with the loaded cartridge in clamping engagement with the tissue "T", the inner surface of locking protuberance 76 is in sliding engagement with the walls of the pusher member 28. However, as can be observed by referring to FIGS. 11 and 12, during the firing stage, advancement of the T-bar 56 in the direction of the arrow 83 will cause pusher member 28 to move interiorly of the staple cartridge 26 so as to drive the staples "S" toward anvil face 24. Because locking head 76 has been cammed into its outer position against the urging of spring element 70, forward movement of T-bar 56 will not be obstructed. However, as can be seen by referring to FIGS. 13, 14, and 15, after the firing step and the retraction of T-bar 56 to the position shown in FIGS. 13 and 15, spring element 70 will urge locking head 76 outwardly into aperture 81 and into the space between members 30 and 32. This is possible because, in this fired position, pusher member 28 has been advanced forwardly of aperture 81 thereby permitting free movement of head portion 76 through the aperture and into the internal space between the members. With the locking head 76 in the position shown in FIG. 15, which is identical to the position shown in FIG. 3, forward movement of T-bar 56 is positively prevented.

It is to be noted that with the novel construction of the apparatus of the invention as previously described, re-approximation of the device can be accomplished while firing, that is, forward movement of T-bar 56, is effectively blocked. This novel feature of the apparatus permits regripping of the tissue after stapling, if such regripping is desired by the surgeon. By way of example, such a requirement for regripping might occur if, after the stapling procedure, the surgeon observes an oozing or leakage of fluid between the joined tissues. In this instance, the surgeon may wish to release the clamped tissue, back the jaws away from the stapled area and then regrip to enable cauterization of the leaking area without interference from the clamping jaws of the apparatus. This novel feature of the apparatus of the present invention is not possible in the prior art devices wherein locking is accomplished by locking the device against approximation as distinguished from locking the device against firing or forward advance of the pusher operating or T-bar 56.

Referring to FIGS. 17 through 29, another embodiment of the stapling apparatus of the invention is there shown. This second embodiment is similar in many respects to that described in the preceding paragraphs and like numerals have been used to describe like components. More particularly, the supporting frame and approximation means of this second form of the invention are identical to those previously described, with the principal difference in the devices being the construction and operation of the locking means.

As in the previously described embodiment, the apparatus of this second form of the invention comprises an elongated supporting frame 14 having first and second spaced walls 16 and 18 defining an interior space 20 (FIG. 19). The anvil portion 22 of the apparatus, which includes a staple-engaging face 24 is disposed at the forward end of the supporting frame 14. Removably receivable within the supporting frame is staple cartridge 26 and a pusher member 28 which are of identical construction and operation to those previously described.

In operating this latest form of the invention, after the tissue has been appropriately positioned between the staple cartridge and the anvil, the approximation means are used to controllably move the staple cartridge 26, along with pusher 28, forwardly of the apparatus into proximity with face 24 of anvil 22. As previously mentioned, the approximation means of this second form of the invention is the same as in the earlier described embodiment and comprises a pair of spaced-apart approximation members 30 and 32 which are disposed between side walls 16 and 18 of the supporting frame. As before, these members are slidably movable from a first retracted position to a forward, approximation, or tissue-clamping position by operation of the handle assembly. In this regard, the approximation means also includes linkage assembly 40 of the same construction and operation as previously described.

After the staple cartridge and its associated pusher member have been moved into close proximity with anvil 22 and in a clamping relationship with tissue "T", as shown in FIG. 21, the apparatus is in condition for the firing or staple-crimping operation. This staple-firing step is accomplished by the operating means of the invention, which means is carried by the supporting frame and here comprises a slightly modified operating member or generally "T" shaped bar 100 which is disposed intermediate operating members 30 and 32 (FIG. 19). As before, operating bar 100 is movable between members 30 and 32 from a first retracted position shown in FIG. 21 to a second advanced or fired position shown in FIG. 24. The operating or T-bar 100 includes a forward face 100b (FIG. 21) which engages wing-like, inwardly bent, forward portions 28a of pusher member 28 so as to urge the pusher member inwardly of the staple cartridge 26 with sufficient force to engage the staples contained within the staple cartridge and drive them forwardly against face 24 of the anvil. In this form of the invention, T-bar 100 is provided with a notch 102 on the upper surface of the head portion of the bar (FIGS. 21 and 22), the purpose of which will presently be described.

During the firing step, handle portions 36 and 38 are squeezed together causing the inboard end of operating link 60 to urge operating member 100 slidably forwardly between members 30 and 32 in the manner shown in FIG. 23. As before, this forward movement of the T-bar will cause pusher member 28 to move inwardly of staple cartridge 26 and into engagement with the staples contained therein.

Referring particularly to FIGS. 18, 22, and 23, it can be seen that the locking means of this latest form of the invention for preventing movement of the modified operating, or T-bar 100, toward its second firing position following the initial firing of the staples is of a substantially different construction than the previously described locking means. More particularly, the locking means here comprises a vertically movable locking pin 106 of the configuration shown in FIGS. 18 and 23. This locking pin is connected to one end 110a of a generally "C" shaped biasing means, or spring 110, which continuously urges downward movement of locking pin 106 toward T-bar 100. When the end 106d of the locking pin is disposed within notch 102 in the manner shown in FIG. 18, the locking pin positively blocks movement of the T-bar 100 forwardly of the apparatus.

As best seen in FIG. 19, the locking means of this latest form of the invention is uniquely disposed between members 30 and 32 and is connected thereto by rivets or other appropriate fasteners 112 in the manner best seen in FIGS. 18 and 22 (see also FIG. 2). Connected to a second end 110b of "C" shaped spring 110 is trigger means here provided as a trigger member 114. Trigger member 114, the purpose of which will presently be described, also comprises a part of the locking means of the invention.

Turning particularly to FIGS. 21 and 22, it is to be noted that trigger member 114, is designed to act upon "C" shaped spring 110 in a manner to urge locking pin 106 upwardly in the direction of the arrow 115 of FIG. 22. For this purpose, trigger member 114 is provided with a sloping forward edge 114a which is so positioned and arranged as to engage the forward portion 28a of the pusher member when the pusher member and staple cartridge are in position within the supporting frame in the manner shown in FIGS. 21 and 22. As indicated by the dotted lines of FIG. 22, prior to insertion of the staple cartridge and its companion, pusher member 28, "C" shaped spring 110 biases trigger member 114 forwardly of the apparatus. However, upon insertion of the staple cartridge and pusher member, trigger member 114 will be urged to the left in the direction of the arrow 117 in the manner shown in FIG. 22. This movement of trigger member 117 exerts a force on "C" shaped spring 110 which causes end 110a thereof to move upwardly, taking with it locking pin 106 which is attached to end 110a of the spring. In this regard, it is to be noted that trigger member 114 is provided with a central aperture 114b within which locking pin 106 is received (see also FIG. 23). It is also to be noted that aperture 114b is specially configured so as to include a ramp face 114c which engages a cooperating ramp face 106c provided on locking pin 106. With this construction, as the trigger member 114 is moved to the left, as shown in FIG. 22, cam surface 114c of trigger member 114 will engage cam surface 106c of pin 106, causing pin 106 to move upwardly in the manner indicated in FIG. 22. As locking member 106 moves upwardly, the lower end of the locking pin will clear notch 102 which is provided in T-bar 100 (FIG. 22).

With the locking pin in the upraised position, it is apparent that the operating or T-bar 100 is free to move toward anvil 22 in the direction of the arrow 119 of FIG. 24. As was the case in the earlier described embodiment, during this firing step wherein T-bar 100 moves forwardly of the supporting frame, face 100b of the T-bar will engage pusher member 28, urging it inwardly of staple cartridge 26 and into engagement with the staples contained therein. Continued forward movement of the T-bar will forcibly drive the staples "S" into face 24 of the anvil causing them to be crimped in a manner to secure together the layers of tissue "T".

Turning now to FIGS. 27 and 28, it is to be noted that after the firing step and as the T-bar 100 is retracted in the direction of the arrow 121 of FIG. 27, the lowered sloping surface portion 106d of the locking pin 106 will engage the inboard edge 100c of T-bar 100 urging upward movement of the locking pin in the direction of the arrow 125. However, as shown in FIG. 29, continued rearward or retraction movement of T-bar 100 will cause end 106d of locking pin 106 to travel to a position where it is superimposed over notch 102. In this position, "C" shaped spring 110 will urge the pin downwardly in the direction of the arrow 127 of FIG. 29 causing the locking pin to securely seat within notch 102 in a manner to block forward motion of the T-bar in a direction toward anvil 22.

With the component parts of the apparatus in the configuration shown in FIG. 29, it is apparent that, as before, the apparatus can be freely used as a clamp or reclamp tissue "T", but so long as locking pin 106 is seated within notch 102, the surgeon will at all times be aware that the cartridge has been fired and that it is no longer possible for him to advance the T-bar 100 in a direction toward the anvil.

The component parts of the locking means of this latest form of the invention can be constructed from a variety of materials. However, "C" shaped spring 110 is preferably constructed from a spring steel while locking members 106 and trigger member 114 are preferably constructed from a metal such as stainless steel.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for simultaneously securing a plurality of surgical staples in tissue comprising:

a supporting frame;

a staple cartridge containing a plurality of staples receivable into said frame;

an anvil mounted on said supporting frame for engagement by said staples;

approximation means for moving said staple cartridge within said supporting frame from a retracted position to a clamping position proximate said anvil;

a pusher member positioned at least partially within said staple cartridge and movable relative thereto into driving engagement with said staples;

an operating member movable within said supporting frame for advancement of said pusher member relative to said staples so as to drive said staples into engagement with said anvil; and locking means for releasably locking said operating member against movement relative to said supporting frame, said locking means including a locking element connected to said approximation means and having a locking protuberance for engaging said approximation means, said locking protuberance moveable from a first position relative to said operating member to a second position, wherein said locking element blocks movement of said operating member toward said staple cartridge.

2. An apparatus as defined in claim 1 in which said approximation means of said apparatus includes a wall having an aperture and in which said locking element comprises a strip of resiliently deformable material having first and second ends, said first end of said deformable material being connected to said wall and said locking protuberance is receivable into said aperture for engagement with said operating member to block movement thereof in a direction toward said staple cartridge.

3. An apparatus as defined in claim 1 in which said operating member is provided with a notch and in which said locking element comprises a locking pin carried by said approximation means for movement between a first retracted position and a second locking position wherein said locking pin is received within the notch provided in said operating member, said locking means further including biasing means for biasing said locking pin toward said second position.

4. An apparatus as defined in claim 3 in which said biasing means comprises a generally "C" shaped spring having first and second ends, said first end being connected to said locking pin, said locking means further including trigger means connected to the second end of said spring the engagement with said pusher member upon insertion of said staple cartridge into said supporting frame so as to move said locking pin toward said first retracted position.

5. An apparatus as defined in claim 4 in which said trigger means comprises a trigger element having first and second ends, said first end being connected to said spring and said second end having a tapered wall for engagement with said pusher member.

6. A surgical apparatus according to claim 1, wherein the locking mechanism is spring biased to the first position.

7. An apparatus for simultaneously emplacing a plurality of surgical staples into tissue comprising:

(a) an elongated supporting frame having walls defining an interior space;

(b) an anvil connected to said supporting frame;

(c) a staple cartridge containing a plurality of staples receivable within said supporting frame, said staple cartridge being movable toward and away from said anvil;

(d) a pusher member carried by said staple cartridge for moving said staples simultaneously toward said anvil;

(e) approximation means including a wall having an aperture carried by said supporting frame for moving said staple cartridge toward said anvil;

(f) operating means carried by said supporting frame for engagement with said pusher member to drive said staples into engagement with said anvil, said operating means comprising an operating bar slidably movable within said supporting frame from a first retracted position to a second staple driving position; and (g) locking means including a locking element connected to said approximation means and movable from a first retracted position to a second locking position, the locking element formed as a strip of resiliently deformable material having first and second ends, said second end having a locking protuberance receivable into said aperture of said wall for preventing movement of said operating bar toward said second staple driving position after driving said staples into pressural engagement with said anvil.

8. An apparatus as defined in claim 7 in which said locking element comprises an elongated spring having first and second ends, said first end being connected to said wall.

9. An apparatus as defined in claim 8 in which said elongated spring continuously biases said protuberance in a direction inwardly of said aperture.

10. An apparatus as defined in claim 9 in which said elongated spring urges said locking protuberance inwardly of said aperture for blocking engagement with said operating bar upon movement of said operating bar into said second position.

11. An apparatus as defined in claim 7 in which said locking protuberance of said locking element is provided with a sloping portion engageable by said pusher member when said staple cartridge and said pusher member are inserted into said supporting frame, said sloping portion being so constructed and arranged to move said locking protuberance outwardly relative to said aperture as said pusher member moves into said supporting frame.

12. An apparatus for simultaneously emplacing a plurality of surgical staples into tissues and organs comprising:

(a) an elongated supporting frame having first and second spaced-apart walls defining an interior space;

(b) an anvil connected to said supporting frame;

(c) a staple cartridge containing a plurality of staples removably receivable within said supporting frame, said staple cartridge being movable toward and away from said anvil;

(d) a pusher member carried by said staple cartridge for moving said staples simultaneously toward said anvil;

(e) approximation means, including spaced-apart walls carried by said supporting frame for moving said staple cartridge toward said anvil;

(f) operating means carried by said supporting frame for engagement with said pusher member to drive said staples into pressural engagement with said anvil, said operating means comprising an operating bar slidably movable between said walls of said approximation means from a first retracted position to a second staple driving position, said operating bar having a notch; and (g) locking means connected to said approximation means for preventing movement of said operating bar toward said second position, said locking means comprising a locking pin disposed between said spaced-apart walls for movement between a first retracted position and a second locking position wherein said locking pin is received within the notch provided in said operating bar, said locking means further including biasing means for biasing said locking pin toward said second position.

13. An apparatus as defined in claim 12 in which said biasing means comprises a generally "C" shaped spring having first and second ends, said first end being connected to said locking pin, said locking means further including trigger means connected to second end of said spring for engagement with said pusher member upon insertion of said pusher member and said staple cartridge into said supporting frame so as to move said locking pin toward said first retracted position.

14. An apparatus as defined in claim 13 in which said trigger means comprises a trigger element having first and second ends, said first end being connected to said spring and said second end having a tapered wall for engagement with said pusher member.

15. An apparatus as defined in claim 14 in which said "C" shaped spring is disposed between said first and second spaced-apart walls of said approximation means.

16. An apparatus as defined in claim 15 in which said operating bar is slidably movable between said spaced-apart walls of said approximation means with said locking pin being superimposed over said notch when said operating bar is in said first position.

17. An apparatus for applying a plurality of surgical fasteners in tissue including:

a supporting frame;

a cartridge containing a plurality of fasteners;

an anvil mounted on said supporting frame for engagement by said fasteners;

an approximation member carried by said supporting frame and configured to move said cartridge relative to said supporting frame from an open position to a clamping position proximate said anvil;

at least one pusher member positioned in said cartridge and movable relative thereto into driving engagement with said fasteners;

an operating member movable within said supporting frame for advancement of said pusher member relative to said fasteners so as to drive said fasteners into engagement with said anvil; and at least one locking element connected to said supporting frame for movement from a first position relative to said operating member to a second position wherein said locking element blocks movement of said operating member toward said cartridge, said approximation member including a wall having an aperture, and wherein said locking element includes a strip of resiliently deformable material having first and second ends, said first end being connected to said wall and said second end having a locking protuberance received in said aperture for engagement with said operating member to block movement thereof in a direction toward said cartridge.

18. An apparatus for emplacing a plurality of surgical staples into tissue comprising:

(a) an elongated supporting frame having walls defining an interior space;

(b) an anvil connected to said supporting frame;

(c) a staple cartridge containing a plurality of staples, said staple cartridge being movable relative to said anvil;

(d) a pusher member positioned in said staple cartridge for moving said staples toward said anvil;

(e) at least one approximation element carried by said supporting frame for moving said staple cartridge toward said anvil;

(f) an operating member carried by said supporting frame for engagement with said pusher member to drive said staples into engagement with said anvil, said operating member comprising a bar slidably movable within said supporting frame from a first retracted position to a second staple driving position; and (g) at least one locking element for preventing movement of said operating bar toward said second position after driving said staples into engagement with said anvil, said locking element movable from a first retracted position to a second locking position wherein said locking element will engage said operating bar to prevent movement thereof toward said second position, and wherein said approximation member further includes a wall having an aperture and in which said locking element includes an elongated spring having first and second ends, said first end being connected to said wall and said second end having a locking protuberance received in the aperture of said wall for engagement with said operating bar to block relative movement thereof.

19. An apparatus as defined in claim 18 in which said elongated spring continuously biases said protuberance in a direction inwardly of said aperture for blocking engagement with said operating bar upon movement of said operating bar into said second position, and wherein said locking protuberance of said locking element is provided with a sloping portion engageable by said pusher member when said staple cartridge and said pusher member are inserted into said supporting frame, said sloping portion being so constructed and arranged to move said locking protuberance outwardly relative to said aperature as said pusher member moves into said supporting frame.

20. An apparatus for simultaneously applying a plurality of surgical staples in tissue including:

a supporting frame;

a staple cartridge containing a plurality of staples removably receivable into said frame;

an anvil mounted on said supporting frame for engagement by said staples;

an approximation member having a wall and an aperture, for moving said staple cartridge within said supporting frame from a retracted position to a clamping position proximate said anvil;

a pusher member connected to said staple cartridge and movable relative thereto into driving engagement with said staples;

an operating member movable within said supporting frame for advancement of said pusher member relative to said staples so as to drive said staples into engagement with said anvil; and a locking mechanism for releasably locking said operating member against movement relative to said approximation member, said locking mechanism comprising at least one strip of resiliently deformable material having first and second ends, said first end being connected to said wall and said second end having a locking proturberance received in said aperture for engagement with said operating member for movement from a first position relative to said operating member to block movement thereof in a direction toward said staple cartridge.

21. An apparatus for simultaneously emplacing a plurality of surgical staples into tissues and organs comprising:

(a) an elongated supporting frame having walls defining an interior space;

(b) an anvil connected to said supporting frame;

(c) a staple cartridge containing a plurality of staples removably receivable within said supporting frame, said staple cartridge being movable toward and away from said anvil;

(d) a pusher member carried by said staple cartridge for moving said staples simultaneously toward said anvil;

(e) an approximation member including an aperture and a wall, said approximation member carried by said supporting frame for moving said staple cartridge toward said anvil;

(f) an operating bar slidably movable within said supporting frame from a first retracted position to a second staple driving position; and (g) a locking mechanism for preventing movement of said operating bar toward said second position after driving said staples into engagement with said anvil, said locking mechanism having an elongated spring having first and second ends, said first end being connected to said wall and said second end having a locking protuberance received in the aperture of said wall for engagement with said operating bar to block movement thereof in a direction toward said staple cartridge.

22. An apparatus as defined in claim 21 in which said elongated spring continuously biases said protuberance in a direction inwardly of said aperture for blocking engagement with said operating bar upon movement of said operating bar into said second position, and wherein said locking protuberance of said locking element is provided with a sloping portion engageable by said pusher member when said staple cartridge and said pusher member are inserted into said supporting frame, said sloping portion being so constructed and arranged to move said locking protuberance outwardly relative to said aperature as said pusher member moves into said supporting frame.

23. A surgical apparatus for simultaneously applying a plurality of staples comprising:

a supporting frame;

an anvil disposed at a distal portion of the supporting frame;

a staple cartridge containing a plurality of staples and a pusher for driving the staples;

a handle mechanism disposed at a proximal portion of the frame, the handle mechanism actuable to advance an elongated firing member to fire the staples in a direction substantially parallel to a direction of movement of the firing member, wherein advancement of the firing member advances the pusher from a proximal position to fire the staples, the pusher remaining in a position distal of the proximal position after firing of the staples;

a locking mechanism cooperable with the staple cartridge, the locking mechanism movable between a first position to block movement of the firing member and a second position to allow advancement of the firing member, the pusher moving the locking mechanism to the second position when the pusher is in the proximal position.

24. A surgical apparatus according to claim 23, further comprising a retaining pin slidable in a longitudinal direction to engage an aperture in the anvil.

25. A surgical apparatus according to claim 23, wherein the locking mechanism is biased in a direction transverse to the direction of movement of the firing member.

26. A surgical apparatus according to claim 23, further comprising an approximation mechanism to approximate the cartridge and anvil, wherein the locking mechanism is positioned on a portion of the approximation mechanism and moves with the approximation mechanism.

27. A surgical apparatus according to claim 23, wherein the handle mechanism is actuable to advance the staple cartridge towards the anvil.

28. A surgical apparatus for simultaneously applying a plurality of staples comprising:

a supporting frame;

an anvil disposed at a distal portion of the supporting frame;

a removable staple cartridge containing a plurality of staples and a pusher for driving the staples, the staple cartridge movable towards the anvil to clamp tissue therebetween;

a handle mechanism at the proximal portion of the frame, the handle mechanism actuable to advance an elongated firing member to fire the staples in a direction substantially parallel to a direction of movement of the firing member, wherein advancement of the firing member advances the pusher from a proximal position to fire the staples, the pusher remaining in a position distal of the proximal position after firing of the staples; and a locking mechanism positioned in the frame and movable from a first position when the cartridge loaded with staples is supported in the frame and a second position when the cartridge is devoid of staples and supported in the frame, the locking mechanism being normally in the second position to block movement of the firing member and movable to the first position by engagement by the pusher.

29. A surgical apparatus according to claim 28, further comprising a retaining pin slidable in a longitudinal direction to engage an aperture in the anvil.

30. A surgical apparatus according to claim 29, wherein the locking mechanism is biased in a direction transverse to the direction of movement of the firing member.

31. A surgical apparatus according to claim 30, further comprising an approximation mechanism to approximate the cartridge and anvil, wherein the locking mechanism is positioned on a portion of the approximation mechanism and moves with the approximation mechanism.

32. A surgical apparatus according to claim 28, wherein the pusher in the proximal position cams the locking member in a direction transverse to the direction of movement of the firing member out of a way of the firing member.

* * * * *